(12) United States Patent
Morrey et al.

(10) Patent No.: US 9,301,844 B2
(45) Date of Patent: Apr. 5, 2016

(54) ACETABULAR CUP PROSTHESIS

(71) Applicant: MAYO FOUNDATION FOR MEDICAL EDUCATION AND RESEARCH, Rochester, MN (US)

(72) Inventors: Bernard Morrey, Rochester, MN (US); Kai-Nan An, Rochester, MN (US); Andrew Thoreson, Kenyon, MN (US); Qingshan Chen, Rochester, MN (US)

(73) Assignee: Mayo Foundation For Medical Education and Research, Rochester, MN (US)

( * ) Notice: Subject to any disclaimer, the term of this patent is extended or adjusted under 35 U.S.C. 154(b) by 0 days.

(21) Appl. No.: 14/556,488

(22) Filed: Dec. 1, 2014

(65) Prior Publication Data

US 2015/0245913 A1 Sep. 3, 2015

Related U.S. Application Data

(63) Continuation of application No. 13/813,059, filed as application No. PCT/US2011/045568 on Jul. 27, 2011, now Pat. No. 8,900,319.

(60) Provisional application No. 61/368,933, filed on Jul. 29, 2010.

(51) Int. Cl.
*A61F 2/34* (2006.01)
*A61F 2/30* (2006.01)
(Continued)

(52) U.S. Cl.
CPC .......... *A61F 2/34* (2013.01); *A61F 2002/30331* (2013.01); *A61F 2002/30494* (2013.01);
(Continued)

(58) Field of Classification Search
CPC . A61F 2/34; A61F 2002/34; A61F 2002/349; A61F 2002/3411; A61F 2002/3412; A61F 2/32; A61F 2002/3414; A61F 2002/3438; A61F 2002/3445; A61F 2002/3446; A61F 2002/3448; A61F 2002/3491
USPC ............................................. 623/22.11–22.39
See application file for complete search history.

(56) References Cited

U.S. PATENT DOCUMENTS 5,310,408 A * 5/1994 Schryver et al. ............ 623/22.37
5,314,487 A * 5/1994 Schryver et al. ............ 623/22.37
(Continued)

FOREIGN PATENT DOCUMENTS

EP 0499475 A2 8/1992
FR 2677878 A1 12/1992
(Continued)

OTHER PUBLICATIONS

Search and Examination Report, dated Dec. 11, 2014, issued by the Intellectual Property Office of Singapore in Application No. 2013005434.
(Continued)

*Primary Examiner* — Alvin Stewart
(74) *Attorney, Agent, or Firm* — Meunier Carlin & Curfman LLC

(57) ABSTRACT

Provided are acetabular cup implant assemblies that can be used in hip replacement surgery. Example assemblies comprise a shell and a liner. The liner can be positioned within a shell. Optionally, the liner can be rotated relative to the shell until the liner is seated in the shell in a position where the liner and shell can be secured to one another. Waveform-shaped features of the shell and liner can guide the relative rotation of the liner and shell. Also provided are methods of seating a liner in shell of an acetabular cup implant assembly.

38 Claims, 11 Drawing Sheets

(51) Int. Cl.
*A61F 2/46* (2006.01)
*A61F 2/32* (2006.01)

(52) U.S. Cl.
CPC ............... *A61F2002/30532* (2013.01); *A61F 2002/30841* (2013.01); *A61F 2002/3275* (2013.01); *A61F 2002/3291* (2013.01); *A61F 2002/3401* (2013.01); *A61F 2002/349* (2013.01); *A61F 2002/3443* (2013.01); *A61F 2002/4641* (2013.01)

(56) References Cited

U.S. PATENT DOCUMENTS

| | | | | |
|---|---|---|---|---|
| 5,549,698 | A * | 8/1996 | Averill et al. | 623/22.22 |
| 5,584,629 | A * | 12/1996 | Bailey et al. | 411/178 |
| 5,609,647 | A * | 3/1997 | K alberer et al. | 623/22.24 |
| 5,653,764 | A * | 8/1997 | Murphy | 623/23.15 |
| 5,658,345 | A * | 8/1997 | Willi | 623/22.26 |
| 5,766,260 | A * | 6/1998 | Whiteside | 623/22.27 |
| 5,782,918 | A * | 7/1998 | Klardie et al. | 606/60 |
| 5,879,401 | A * | 3/1999 | Besemer et al. | 623/22.28 |
| 5,881,443 | A * | 3/1999 | Roberts et al. | 29/446 |
| 5,931,870 | A * | 8/1999 | Cuckler et al. | 623/22.21 |
| 5,935,175 | A * | 8/1999 | Ostiguy et al. | 623/22.28 |
| 5,976,148 | A * | 11/1999 | Charpenet et al. | 606/91 |
| 5,989,293 | A * | 11/1999 | Cook et al. | 623/22.29 |
| 6,004,322 | A * | 12/1999 | Bernstein | 606/305 |
| 6,129,765 | A * | 10/2000 | Lopez et al. | 623/22.15 |
| 6,152,961 | A * | 11/2000 | Ostiguy et al. | 623/22.28 |
| 6,162,256 | A * | 12/2000 | Ostiguy et al. | 623/22.26 |
| 6,231,611 | B1 * | 5/2001 | Mosseri | 623/22.12 |
| D446,859 | S * | 8/2001 | Hurson | D24/156 |
| 6,334,875 | B1 * | 1/2002 | Keller | 623/22.28 |
| 6,602,293 | B1 * | 8/2003 | Biermann et al. | 623/23.5 |
| 6,610,097 | B2 * | 8/2003 | Serbousek et al. | 623/22.24 |
| 6,626,947 | B2 * | 9/2003 | Lester et al. | 623/22.23 |
| 6,652,535 | B2 * | 11/2003 | Kvarnstrom et al. | 606/105 |
| 6,719,796 | B2 * | 4/2004 | Cohen et al. | 623/17.15 |
| 7,044,974 | B2 * | 5/2006 | Garber et al. | 623/22.21 |
| 7,074,241 | B2 * | 7/2006 | McKinnon | 623/22.24 |
| 7,294,150 | B1 * | 11/2007 | Mandell et al. | 623/22.28 |
| RE40,090 | E * | 2/2008 | Whiteside | 623/22.19 |
| 8,002,842 | B2 * | 8/2011 | Ronk | 623/22.24 |
| 8,123,815 | B2 * | 2/2012 | Meridew et al. | 623/22.29 |
| 8,163,029 | B2 * | 4/2012 | Lewis et al. | 623/22.38 |
| 8,177,851 | B2 * | 5/2012 | Drescher | 623/22.29 |
| 8,211,184 | B2 * | 7/2012 | Ries et al. | 623/22.21 |
| 8,308,810 | B2 * | 11/2012 | Meridew | 623/22.19 |
| 2002/0040245 | A1 * | 4/2002 | Lester et al. | 623/22.23 |
| 2002/0143402 | A1 * | 10/2002 | Steinberg | 623/22.16 |
| 2003/0050705 | A1 * | 3/2003 | Cueille et al. | 623/22.24 |
| 2003/0074079 | A1 * | 4/2003 | McTighe et al. | 623/22.42 |
| 2003/0153982 | A1 * | 8/2003 | Pria | 623/22.24 |
| 2005/0240276 | A1 * | 10/2005 | Shea et al. | 623/22.28 |
| 2005/0246031 | A1 * | 11/2005 | Frederick et al. | 623/22.29 |
| 2006/0173550 | A1 * | 8/2006 | Ragbir | 623/22.46 |
| 2006/0217814 | A1 * | 9/2006 | Lambert et al. | 623/22.17 |
| 2006/0217815 | A1 * | 9/2006 | Gibbs et al. | 623/22.17 |
| 2007/0028710 | A1 * | 2/2007 | Kraus et al. | 74/400 |
| 2007/0038305 | A1 * | 2/2007 | Leyen et al. | 623/22.15 |
| 2007/0043446 | A1 * | 2/2007 | Murray | 623/22.12 |
| 2007/0106391 | A1 * | 5/2007 | Ronk | 623/22.21 |
| 2007/0106392 | A1 * | 5/2007 | Servidio et al. | 623/22.28 |
| 2007/0203583 | A1 * | 8/2007 | Slone | 623/22.28 |
| 2007/0219640 | A1 * | 9/2007 | Steinberg | 623/22.12 |
| 2008/0140215 | A1 * | 6/2008 | Gladdish et al. | 623/22.21 |
| 2009/0005879 | A1 * | 1/2009 | Tuke et al. | 623/22.24 |
| 2009/0088864 | A1 * | 4/2009 | Lewis et al. | 623/22.21 |
| 2009/0088865 | A1 * | 4/2009 | Brehm | 623/22.21 |
| 2009/0171464 | A1 * | 7/2009 | Imhof | 623/22.21 |
| 2009/0287312 | A1 * | 11/2009 | Berger et al. | 623/22.29 |
| 2010/0049327 | A1 * | 2/2010 | Isch et al. | 623/19.12 |
| 2010/0318192 | A1 * | 12/2010 | Laffay et al. | 623/22.21 |
| 2011/0009975 | A1 * | 1/2011 | Allen et al. | 623/22.24 |
| 2011/0015753 | A1 * | 1/2011 | Meridew | 623/22.24 |
| 2012/0004733 | A1 * | 1/2012 | Hodorek et al. | 623/19.11 |
| 2012/0016486 | A1 * | 1/2012 | Yokoo | 623/22.24 |
| 2012/0095569 | A1 * | 4/2012 | Kellar et al. | 623/23.43 |
| 2012/0179270 | A1 * | 7/2012 | Nevins et al. | 623/22.35 |
| 2012/0180300 | A1 * | 7/2012 | Gradel | 29/447 |
| 2012/0185059 | A1 * | 7/2012 | Vankoski et al. | 623/22.24 |
| 2013/0131823 | A1 * | 5/2013 | Morrey et al. | 623/22.24 |
| 2013/0184831 | A1 * | 7/2013 | McMinn | 623/20.35 |
| 2013/0268083 | A1 * | 10/2013 | McMinn | 623/22.24 |

FOREIGN PATENT DOCUMENTS

| | | |
|---|---|---|
| FR | 2686791 A1 | 8/1993 |
| JP | 568690 | 3/1993 |
| JP | 2010520027 | 6/2010 |
| WO | 9405234 A1 | 3/1994 |
| WO | 0167999 A2 | 9/2001 |
| WO | 2007108848 A1 | 9/2007 |
| WO | 2008109143 A1 | 9/2008 |

OTHER PUBLICATIONS

Official Action, mailed Mar. 23, 2015, issued by the Japan Patent Office in corresponding Japanese Patent Application No. 2013-521946.

* cited by examiner

ACETABULAR CUP PROSTHESIS

CROSS REFERENCE TO RELATED APPLICATIONS

This application is a continuation of U.S. patent application Ser. No. 13/813,059, filed Jan. 29, 2013, which is the National Phase (371) of PCT Application No. US2011/045568, filed Jul. 27, 2011, which claims priority to U.S. Provisional Application 61/368,933, filed Jul. 29, 2010, all of which are incorporated by reference herein in their entirety.

TECHNICAL FIELD

The present application relates to hip implant devices and particularly to acetabular cup assemblies for use in hip surgery.

BACKGROUND

Total hip replacement surgery typically entails removal and replacement of the femoral head and the acetabulum. Acetabular cup assemblies for replacement of the acetabulum may include a shell portion and a liner insert that can be positioned within the shell.

In practice, surgeons implanting the shell and insert often have a difficult time aligning the two components. Such difficulties can result from the relatively small working space available to the surgeon during a hip replacement procedure, which may prevent a complete view of the replacement components.

SUMMARY

Provided are acetabular cup implants comprising shells and liners. An example shell may have an outer shell surface adapted for seating in a subject's pelvic bone, an inner shell surface, a shell opening, and a rim positioned peripheral to the shell opening and having a waveform shape. The waveform shape has at least one wave peak and at least one wave valley.

The liners are adapted for insertion into the shell. An example liner has an outer liner surface, an inner liner surface, a liner opening, and a rim positioned peripheral to the liner opening and having a waveform shape. The waveform shape of the liner has at least one wave peak and at least one wave valley. At least a portion of the liner rim rests on at least a portion of the shell rim upon insertion of the liner into the shell.

When the liner is inserted into the shell at least one liner wave peak can rest within at least one shell wave valley. Also, when the liner is inserted into the shell at least one liner wave peak can rest on at least one shell wave peak. Moreover, at least one liner wave peak can rest on the shell rim waveform shape at a location between at least one shell wave peak and at least one shell wave valley.

When the liner is inserted in a position where the liner peak is not seated within a shell valley the liner may be rotated relative to the shell. For example, the liner can be rotated relative to the shell such that the liner wave peak moves from its resting position on the shell wave peak, or from its resting position between the shell wave peak and the shell wave valley, into a position where the liner wave peak rests within a shell wave valley. Therefore, the liner and shell can be rotated until the liner waveform shape and the shell waveform shape integrate wherein one or more peaks of the liner and shell are seated within one or more valleys of the shell or liner respectively. In this position, the waveform geometry of the shell and liner are substantially congruent.

The shell and the liner rim waveform shapes can each comprise a plurality of wave peaks and wave valleys. Each shell peak and shell valley may be spaced equally about the shell rim from each neighboring shell peak or shell valley. In some examples, the shell can have 2, 3, 4, 5, 6, 7, 8, 9 or 10 or more shell peaks.

Each shell peak is separated from its neighboring shell peak on the shell rim by an angle that may be measured relative to an axis of the shell that is perpendicular to the shell opening. Optionally, the angle, and therefore the separation between each peak, is about 180, 120, 90, 72, 60, 51.4, 45, 40 or 36 degrees.

Example shells can also have 2, 3, 4, 5, 6, 7, 8, 9, 10 or more shell valleys. Each shell valley is separated from its neighboring shell valley on the shell rim by an angle that may be measured relative to an axis of the shell that is perpendicular to the shell opening. Optionally, the angle, and therefore the separation between each peak, is about 180, 120, 90, 72, 60, 51.4, 45, 40 or 36 degrees.

Similar to the shell peaks and valleys, each liner peak and each liner valley can be spaced equally about the liner rim from each neighboring liner peak or liner valley. Optionally, there are 2, 3, 4, 5, 6, 7, 8, 9, 10 or more liner peaks. Moreover, each liner peak is separated from its neighboring liner peak on the liner rim by an angle that may be measured relative to an axis of the liner that is perpendicular to the liner opening. Optionally, the angle, and therefore the separation between each peak, is about 180, 120, 90, 72, 60, 51.4, 45, 40 or 36 degrees.

Example liners can also have 2, 3, 4, 5, 6, 7, 8, 9, 10 or more liner valleys. Each liner valley is separated from its neighboring liner valley on the liner rim by an angle that may be measured relative to an axis of the liner that is perpendicular to the shell opening. Optionally, the angle is about 180, 120, 90, 72, 60, 51.4, 45, 40 or 36 degrees.

The described acetabular cup inserts can further comprise a locking mechanism that is engageable upon the seating of the liner and shell in a position where one or more liner peaks rests within one or more shell valleys. Engagement of the locking mechanism can secure the liner in the shell. Optionally, the locking mechanism is not capable of engagement when a liner peak rests on a shell peak, or when a liner peak rests between a shell peak and a shell valley.

When the liner is inserted into a position within the shell where the wave peaks of the waveform shape of the liner rim are not aligned with the valleys of the waveform shape of the shell rim, the liner can be rotated relative to the shell until the peaks of the liner rim waveform shape rest in the valleys of the shell rim waveform shape. Once rotated into this seated position, the shell and liner can be secured together using the locking mechanism.

Also provided are methods of seating a liner for an acetabular prosthetic assembly within its complementary shell. An example method comprises providing an acetablular cup assembly. The assembly comprises a liner and a shell. The shell can comprise an outer shell surface adapted for seating in a subject's pelvic bone, an inner shell surface, a shell opening, and a rim positioned peripherally to the shell opening and having a waveform shape. The waveform shape can have at least one wave peak and at least one wave valley.

The liner is adapted for insertion into the shell. The liner comprises an outer liner surface, an inner liner surface, a liner opening, and a rim positioned peripherally to the liner opening and having a waveform shape. The waveform shape has at least one wave peak and at least one wave valley. The liner may be inserted into the shell such that at least a portion of the liner rim rests on at least a portion of the shell rim.

For example, at least one liner wave peak can rest on at least one shell wave valley when the liner is inserted into the shell. In another example, at least one liner wave peak rests on at least one shell wave peak when the liner is inserted into the shell. Moreover, at least one liner wave peak can rest on the shell rim waveform at a location between at least one shell wave peak and at least one shell wave valley when the liner is inserted into the shell.

When the liner is inserted into the shell in a position wherein the liner peak is not seated within the shell valley, the liner can be rotated relative to the shell such that the liner wave peak moves from its resting position on the shell wave peak, or from its resting position between the shell wave peak and the shell wave valley, into a position where the liner wave peak rests within a shell wave valley. In this position, a locking mechanism can be engaged to secure the liner to the shell wherein the shell wave peak is located within the shell wave valley. In this position, the waveform geometry of the shell and liner are substantially congruent.

These and other features and advantages of the present invention will become more readily apparent to those skilled in the art upon consideration of the following detailed description and accompanying drawings, which describe both the preferred and alternative embodiments of the present invention.

DETAILED DESCRIPTION

Figure 1A:
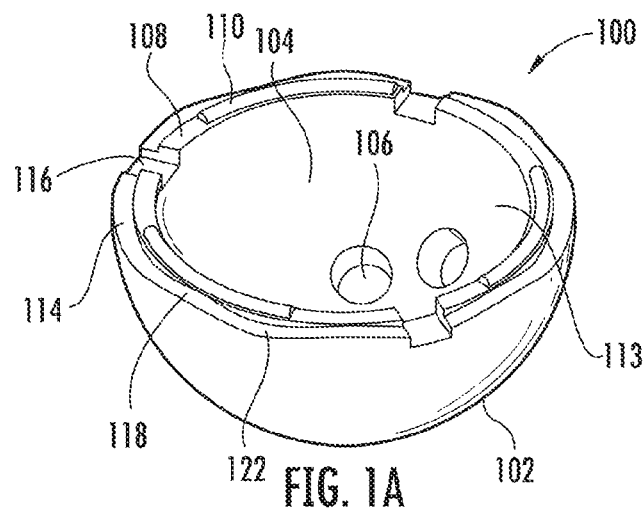
FIGS. 1A-C are schematic illustrations of example shells of an acetabular cup assembly.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," and "the," include plural referents unless the context clearly dictates otherwise.

The term "comprising" and variations thereof as used herein are used synonymously with the term "including" and variations thereof and are open, non-limiting terms.

Total hip replacement surgery typically entails removal and replacement of the femoral head and the acetabulum. Acetabular cup assemblies for replacement of the acetabulum may include a shell portion and a liner insert that can be positioned within the shell.

In practice, surgeons implanting the shell and insert often have a difficult time aligning the two components. Such difficulties can result from the relatively small working space available to the surgeon during a hip replacement procedure, which may prevent a complete view of the replacement components. Acetabular cup assemblies that can effectively be inserted into a patient under these potentially difficult surgical conditions are desirable.

Provided are acetabular cup implant assemblies that can be used in hip replacement surgery. Example assemblies comprise a shell and a liner. The liner can be positioned within a shell. Optionally, the liner can be rotated relative to the shell until the liner is seated in the shell in a position where the liner and shell can be secured to one another. Waveform-shaped features of the shell and liner can guide the relative rotation of the liner and shell. Also provided are methods of seating a liner in a shell of an acetabular cup implant assembly.

An example shell may have an outer shell surface adapted for seating in a subject's pelvic bone, an inner shell surface, a shell opening, and a rim positioned peripheral to the shell opening and having a waveform shape. The waveform shape has at least one wave peak and at least one wave valley. A wave peak or peaks are the point or points of the waveform nearest to the shell opening. Similarly, a wave valley or valleys are the point or points of the waveform furthest from the shell opening.

The liners are adapted for insertion into the shell. An example liner has an outer liner surface, an inner liner surface, a liner opening and a rim positioned peripheral to the liner opening and having a waveform shape. The waveform shape of the liner has at least one wave peak and at least one wave valley. A wave peak or peaks are the point or points of the waveform nearest to the liner opening. Similarly, a wave valley or valleys are the point or points of the waveform furthest from the liner opening. At least a portion of the liner rim rests on at least a portion of the shell rim upon insertion of the liner into the shell.

When the liner is inserted into the shell at least one liner wave peak can rest within at least one shell wave valley. Optionally, the shell and liner waveforms comprise the same number of peaks and valleys. Optionally, the angle between each peak of the shell and liner waveforms is the same. When the liner is inserted into the shell at least one liner wave peak can also rest on at least one shell wave peak. Moreover, at least one liner wave peak can rest on the shell rim waveform shape at a location between at least one shell wave peak and at least one shell wave valley.

When the liner is inserted in a position where the liner peak is not seated within a shell valley, the liner may be rotated relative to the shell. For example, the liner can be rotated relative to the shell such that the liner wave peak moves from its resting position on the shell wave peak, or from its resting position between the shell wave peak and the shell wave valley, into a position where the liner wave peak rests within a shell wave valley. Therefore, the liner and shell can be rotated until the liner waveform shape and the shell waveform shape integrate such that one or more peaks of the liner and shell are seated within one or more valleys of the shell or liner respectively.

Figure 1B:
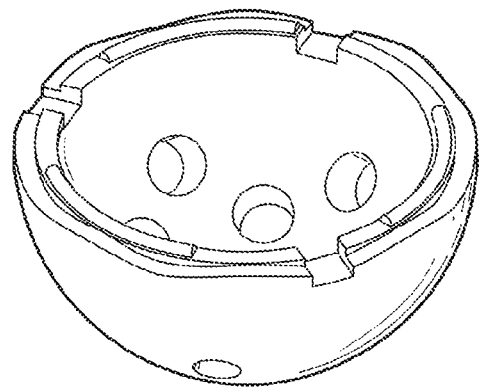
Figure 1C:
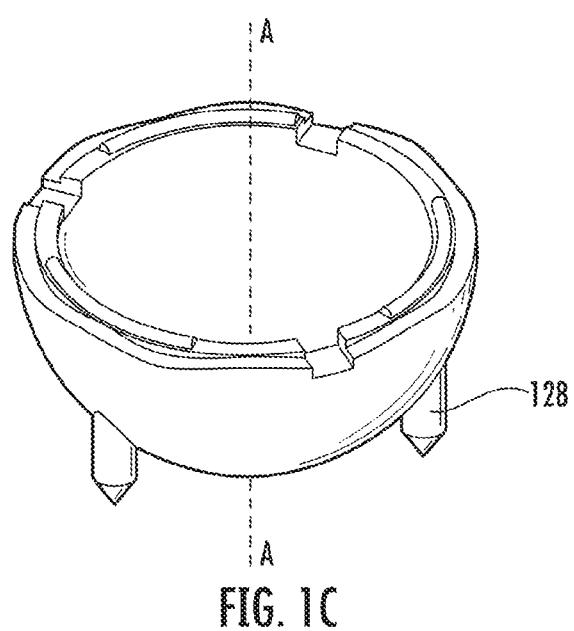

Referring to FIGS. 1A-C, an example shell 100 of an acetabular cup assembly is illustrated. The shell 100 is sized and shaped to be positioned in a surgically prepared acetabular site. The shell 100 can comprise metal or metal alloy, such as titanium or a titanium alloy. Optionally, the shell is machined from as single piece of metal or metal alloy. Optionally, the shell can comprise an assembly of separate pieces of metal or metal alloy.

The shell 100 has an outer surface 102 that can be seated and fixed in the acetabular surgical site. The outer surface 102 is convex such that when properly seated it may approximate the shape of the surgical site. Optionally, the outer surface 102 is coated with a porous material that enhances bonding of the shell to pelvic bone at the surgical site. The porous material coating may comprise titanium or a titanium alloy. The shell 100 may also be cemented into the acetabular surgical site using appropriate surgical or bone cement.

The shell can further comprise several holes 106 that allow one or more fixation device, such as a screw, to be advanced through the shell and into the pelvic bone. By gaining purchase in the pelvic bone, each fixation device can help secure the shell in a desired position in the pelvis. In some example shells, a combination of a fixation device, cement, and bone in-growth into porous material coated on the shell can secure the shell in the pelvis.

The shell 100 can also comprise one or more spikes 128. The spikes 128 extend from the outer surface 102 of the shell. The spikes 128 can penetrate pelvic bone to provide fixation of the shell to the pelvis. Optionally, as shown in FIG. 1C, no holes 106 are used with shells that comprise spikes 128.

The inner surface 104 of the shell 100 is concave and may be sized and shaped to for seating of a liner insert 300. Liner inserts are also referred to herein as liners. Example liners 300 are shown in FIGS. 3A, 3B, 4A-D and 7A-I. The inner surface 104 of the shell 100 can be made from the same material as the outer surface 102. Optionally, the shell 100 can be machined from a single piece of metal comprising titanium or a titanium alloy. As discussed previously, the outer surface 102 can be coated with a porous coating, which can also comprise titanium or a titanium alloy.

The shell 100 can further comprise an inner rim 108 and an outer rim 114. The inner rim 108 and outer rim 114 can both be arcuate or ring shaped. In this way, the rims can frame the major opening 113 that will accept the shell liner 300. As with the inner and outer surfaces (102 and 104 respectfully), the rim portions (108 and 114) of the shell can be titanium or an alloy comprising titanium. The outer rim 114 can have a waveform shape with peaks 118 and valleys 122. The waveform can have a variable number of peaks and valleys as described in greater detail below with regard to FIGS. 6A-I.

One or more slots 116 for disengaging the liner 300 for the shell 100 can be positioned about the rim of the shell. A slot 116 can extend through the outer rim 114 or through both the outer 114 and inner 108 rims. A slot 116 may prevent the outer rim 114 from completing a full ring shaped path. Therefore, the outer rim may comprise two or more arcuate segments depending on the number of slots 116.

A slot 116 has an opening defined by the outer surface 102 of the shell. For example, if the slot is rectangular or square the bottom and side surfaces of the slot opening can be defined by the outer surface 102 of the shell. The top of the opening can be defined by a portion of the liner when it is seated within the shell. For example, as shown in FIG. 5B, the slot can be defined by the other shell surface 102 and the waveform shape of the liner 300.

Similarly, the inner rim 108 may be disrupted by one or more slots 116. The slots 116 may prevent the inner rim 108 from completing a full ring shaped path. Therefore, the outer rim may also comprise two or more arcuate segments depending on the number of slots 116.

The slots 116 may be sized and shaped to allow insertion of a tool or instrument that can provide leverage for separating the liner 300 from the shell 100. For example, when the liner 300 is seated within the shell 100, a tool with a flattened portion can be inserted into a slot 116 and under the back side of the liner 300. The tool can then be manipulated by an operator to cause, or to instigate, separation of the seated liner from the shell.

The inner rim 108 may also include a locking mechanism 110. The locking mechanism 110 protrudes from the horizontal plane of the inner rim 108. The locking mechanism 110 can be arcuate or ring shaped. For example, if the inner rim 108, including the locking mechanism 110, is disrupted by one or more slots 116, then the locking mechanism 110 may comprise two or more arcuate segments.

The cross-sectional shape of the locking mechanism can vary. In the examples shown, the locking mechanism 110 has a hump cross-sectional shape. As shown in FIG. 2C, for example, the cross sectional shape of the locking mechanism 110 is a hump protruding from the inner rim 108. More specifically, the cross-sectional shape of the locking mechanism 110 can be partially circular with the center 230 of the circular portion located above the horizontal plane of the inner rim 108.

By having the center 230 of the circular portion above the inner rim plane, a complementary portion of a liner 300 can lock onto the locking mechanism 110. For example, the locking mechanism 110 of the shell can mate with a groove 326 of the liner 300. The groove 326 is shown, for example, in FIGS. 4B-D.

The groove 326 can comprise a circular cross sectional void that is complementary to the hump shape of the locking mechanism 110. The center of the circular cross section of the groove 326 can have a center 327 that is offset from the plane $P_1$-$P_1$ shown in FIG. 4C. When the groove 326 and the locking mechanism 110 have complementary shapes with offset centers, a lip is produced on the inner and outer edges of the groove opening that can mate with an indention produced at the junction of the locking mechanism 110 and the inner rim 108. These complementary shapes help lock the liner 300 to the shell 100 when the liner 300 is seated in the shell 100 for use.

Referring again to FIGS. 1A-C, the outer rim 114 has a waveform shape. The waveform comprises peaks 118 and valleys 122. The angle between successive peaks 118 or valleys 122 can be determined in reference to the central axis of the shell A-A shown in FIG. 1C and in FIGS. 6A-I.

Figure 6A:
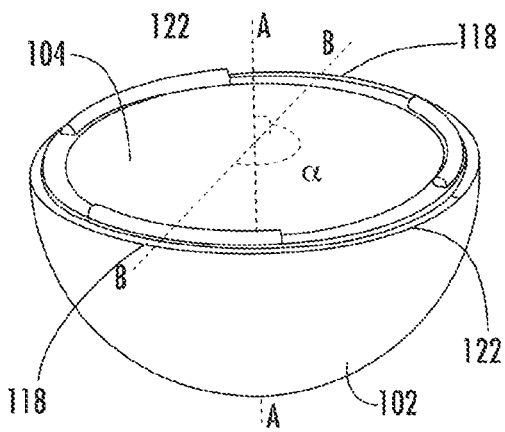
FIGS. 6A-I are schematic illustrations showing example shells having rims with a waveform shape.
Figure 6B:
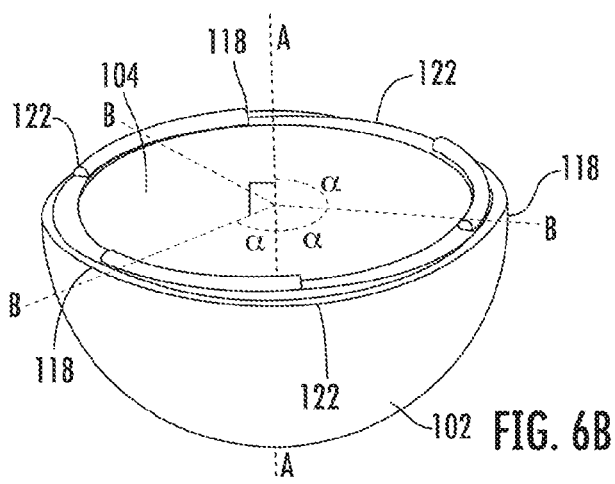
Figure 6C:
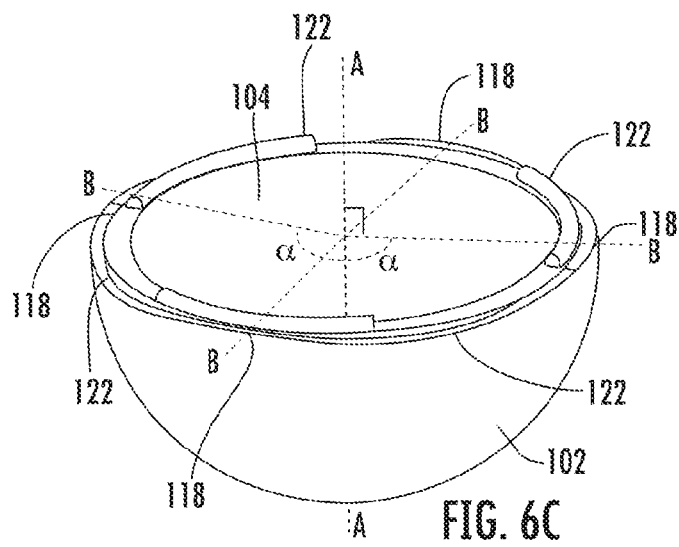
Figure 6D:
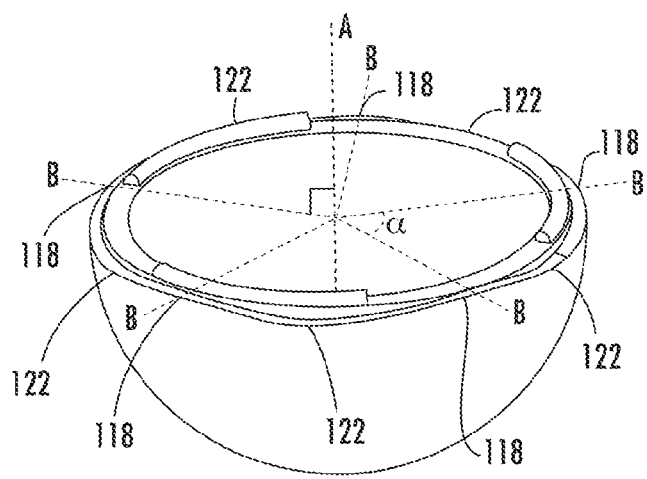
Figure 6E:
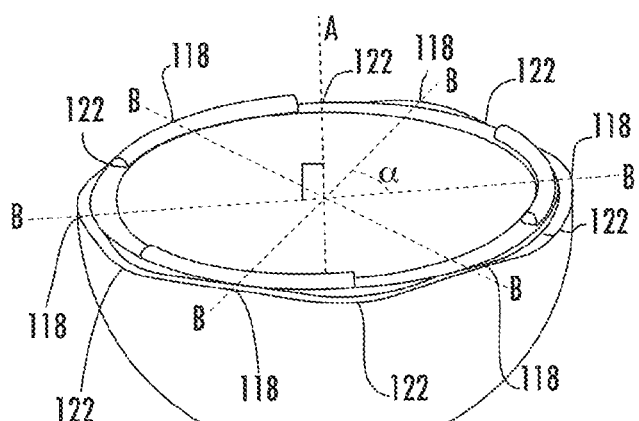
Figure 6F:
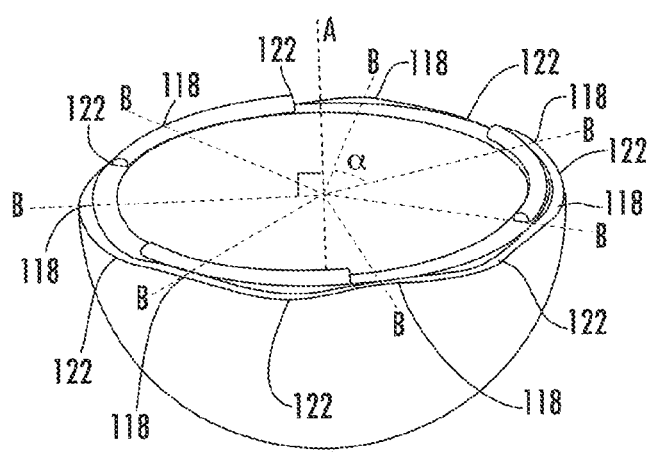

Referring in particular to FIGS. 6A-I, spokes B drawn perpendicular to the axis A-A intersect the apex of each wave peak. The angle ($\alpha$) denotes the angle between peaks. For example, in FIG. 6A, two peaks 118 are shown with an angle ($\alpha$) of 180° between each. In FIG. 6B, a third wave peak is added with the angle ($\alpha$) between each peak of 120°. In each successive example, shown in FIGS. 6C-6I, an additional peak is shown. The angle ($\alpha$) between each peak can be determined by dividing 360° by the total number of peaks.

Figure 6G:
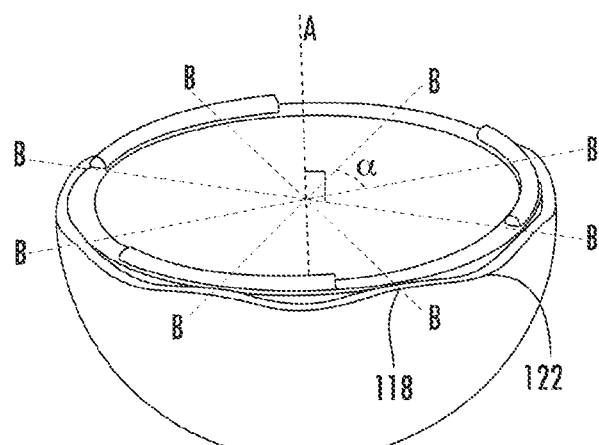
Figure 6H:
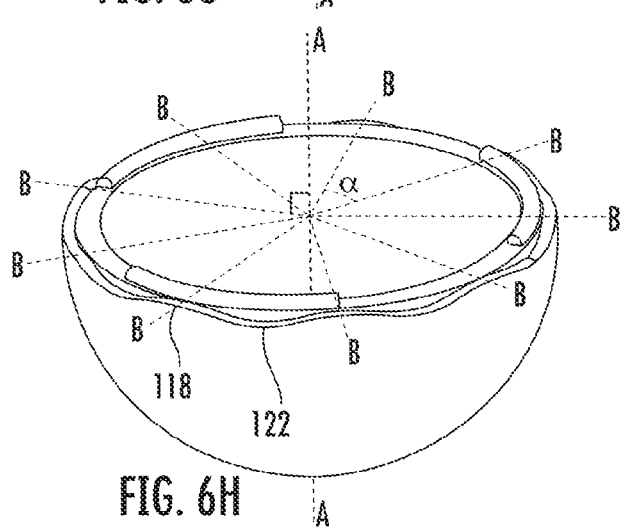
Figure 6I:
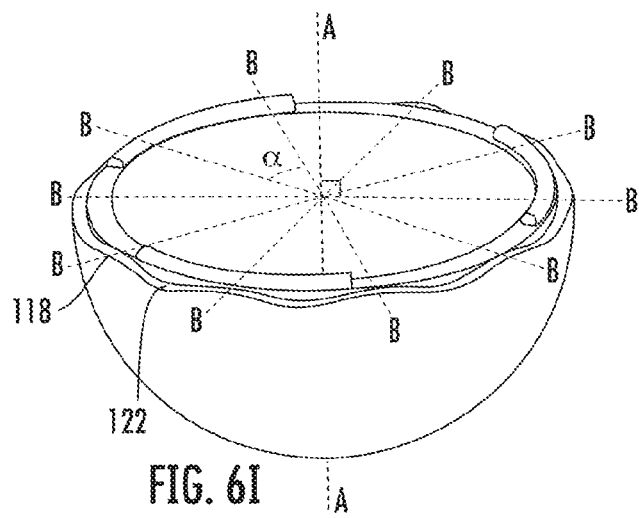

Thus, by way of example, FIG. 6G shows an example shell with eight peaks. By dividing 360° by the total number of peaks, eight, the angle (α) between each peak is determined to be 45°.

Figure 3A:
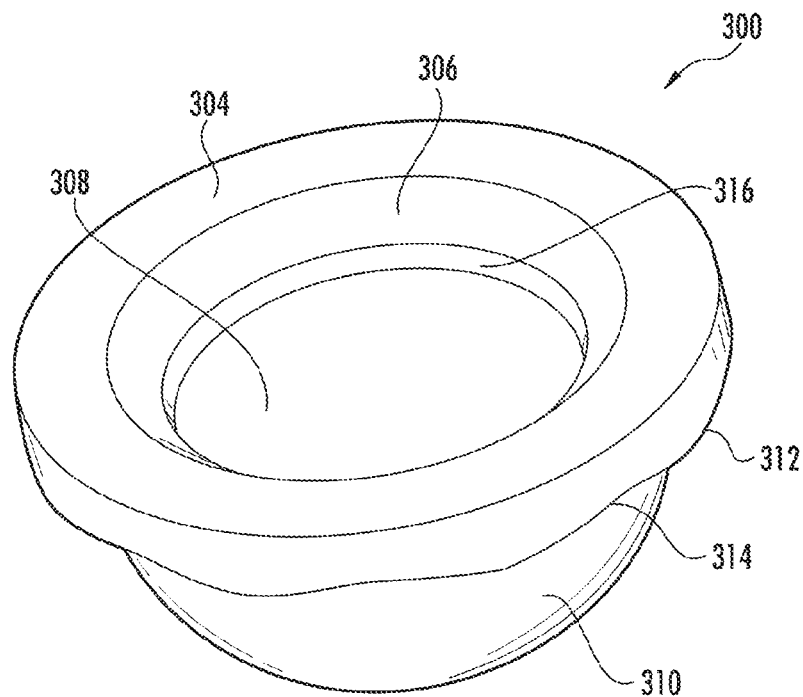
FIGS. 3A and 3B are schematic illustrations of example liners of an acetabular cup assembly.

The number of peaks can vary. Optionally, there can be two or more peaks. For example, there can be 2, 3, 4, 5, 6, 7, 8, 9, 10 or more peaks and the angles between the peaks can be about 180, 120, 90, 72, 60, 51.4, 45, 40, or 36 degrees. Moreover, it is not necessary for the peaks to be uniformly distributed as shown in FIGS. 1A-C and in FIG. 6. In this regard, the angle between the peaks can vary. Therefore, a shell can have a waveform with multiple peaks wherein the angles between one or more wave peaks is the same or differs. In examples where the angle varies, the angle between each peak can vary from less than one degree to greater than 359 degrees. When the angle between the peaks and valleys are the same the peaks and valleys and are uniformly distributed in the shell as shown in FIGS. 1A-C and in FIGS. 6A-I, and in the liner as shown in FIGS. 3A and B and in FIGS. 7A-I. In these aspects, the positioning options wherein the liner waveform is substantially congruent with the shell waveform are increased.

Figure 2A:
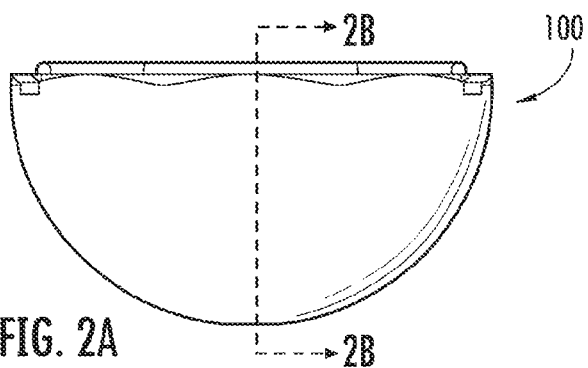
FIG. 2A is a schematic illustration of an example shell of an acetabular cup assembly.
Figure 2B:
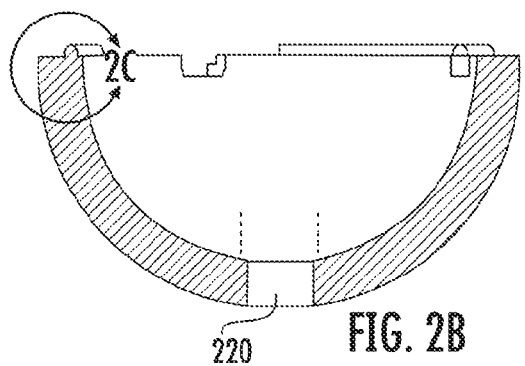
FIG. 2B is schematic illustration of the shell shown in FIG. 2A taken across cross section 2B-2B.
Figure 2C:
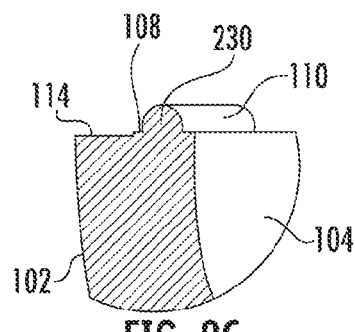
FIG. 2C is a schematic illustration showing portions of FIG. 2B in greater detail.

FIGS. 2A-2D are schematic illustrations showing portions of an example shell in further detail. FIG. 2B is a schematic cross sectional view taken across plane B-B of FIG. 2A. FIG. 2B shows a hole 220, which may be threaded, positioned through the wall of the shell 100 at the bottom of the concave inner surface 104 of the shell. If the hole 220 is threaded, it can be used to accept a tool with a complementary thread pattern for assisting with insertion of the shell into a surgical site.

Figure 2D:
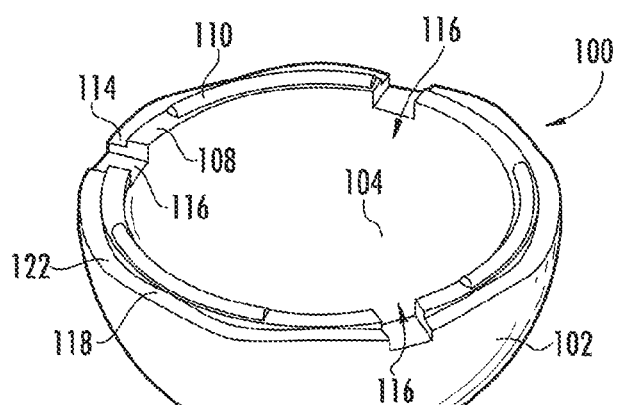
FIG. 2D is a schematic illustration of an example shell of an acetabular cup assembly.

FIG. 2C is a detailed illustration of the circular indicated section from FIG. 2B showing a cross section of the locking mechanism 110 having a center 230. FIG. 2D is a schematic perspective view of an example shell 100 showing the inner surface 104, the outer surface 102, the outer rim 114 having a waveform with multiple peaks 118 and valleys 122, and the inner rim 108 having a locking mechanism 110 protruding from the place of the inner rim 108. FIG. 2D further shows three slots 116 for tool insertion and disengagement of the mated shell and liner. In this configuration, the slots 116 divide the inner 108 and outer rims 114 into three segments. Each segment comprises an arcuate locking mechanism 110. The number of slots 116, peaks 118, valleys 122, segments, locking mechanisms 110 can vary.

Referring now to FIGS. 3A and B, example liners are illustrated. Referring to FIG. 3A, the liner 300 is sized and shaped for seating within the shell 100. The liner comprises an outer surface 310 and in inner surface 308. Portions of the outer surface 310 contact the inner surface 104 of the shell when the liner 300 is seated within the shell. Optionally, the outer surface 310 is highly congruent with the inner surface 104 to distribute stress evenly between the shell 100 and liner 300 components during use.

The inner surface 308 is also configured to articulate with a portion of the femoral head of the femur or the femoral portion of a stem implant used for hip replacement. The liner component can comprise polyethylene. For example, the liner component can be made of ultra high molecular weight polyethylene. Ultra high molecular weight polyethylene is commonly used in hip replacement prostheses and generally comprises polyethylene that has been at least partially cross linked.

The outer diameter of the liner can also vary. For example, the outer diameter of the liner can vary from about 32 millimeters (mm) to about 50.5 mm. Landmarks for the inner and outer diameters of the liner are shown in FIG. 4D. Referring to FIG. 4D, in some examples, the liner outer rim 313 has a thickness (D). Optionally, the thickness may be about or between 1 mm or 2 mm. For example (D) may optionally be 1.3 mm. The thickness (C) of the inner liner rim 325 may be between about or between 1 mm or 2 mm. Optionally, the thickness of inner and outer rims is constant across all sizes of liner inner diameter and outer diameter of the liner.

Figure 2E:
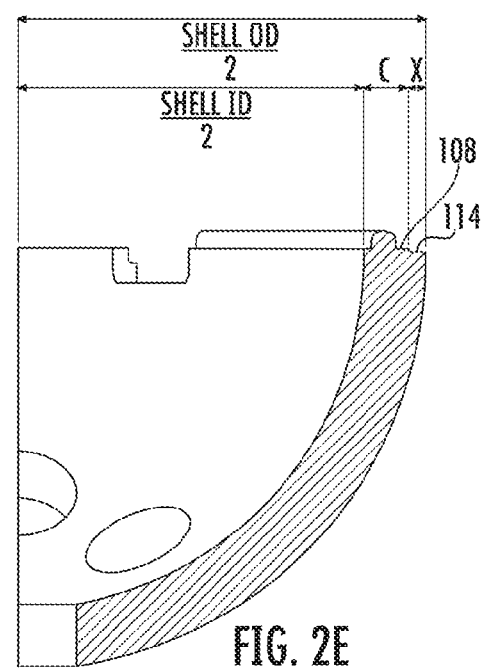
FIG. 2E is a schematic illustration showing portions of an example shell of an acetabular cup assembly.

The varying sizes of the liner 300 can be matched with a variety of shell 100 sizes. Landmarks for the inner and outer diameters of an example shell are shown in FIG. 2E. Referring to FIG. 2E, in some examples, the shell outer rim 114 has a thickness (x). Optionally, the thickness may be about or between 1 mm or 2 mm. For example (x) may optionally be 1.3 mm. The thickness (C) of the inner shell rim 108 may be between about or between 1 mm or 2 mm Optionally, the thickness of inner and outer rims is constant across all sizes of liner inner diameter and outer diameter of the shell.

The inner diameter (ID) of the shell 100 can vary, for example, from about 32 mm to about 50.5 mm. The outer diameter (OD) of the shell 100 can vary, for example, from about 40 mm to about 60 mm. The liner 300 can have an inner diameter (ID) from about 22 mm to about 32 mm. Optionally, the inner diameter can be 22, 28, 32 or 36 mm. The outer diameter (OD) of the liner can vary from about 32 to 50 mm.

Table 1 shows example, non-limiting, combinations of sizes (in millimeters) for liners 100 and corresponding shells 300 based on inner and outer diameter. Other size combinations of liners and shells and liner/shell combinations, beyond those described in Table 1, can be used. For example, a larger liner and/or shell inner diameter (ID) may be desired for use with larger femoral head components. An appropriate liner and shell size can be selected from those listed in Table 1, or from other sizes based on a variety of medical/surgical considerations. For example, a surgeon or other medical professional can determine appropriate shell and liner sizes, and combinations thereof, by evaluating the medical situation in which the devices will be used.

The liner can be configured to articulate with a variety of femoral heads with differing femoral head diameter. The thickness of the liner polyethylene may optionally be at least 6 mm. For example, the liner can be sized and shaped to articulate with femoral heads having a diameter from about 22 millimeters (mm) to 36 mm.

Optionally, the liner outer diameter (OD) is equal in size to the shell inner diameter (ID). The shell OD can be equal to the shell ID+2*C+2*x. The liner rim OD, can be equal to the liner OD+2*C+2*d.

TABLE 1

| Liner ID | Liner OD | Shell OD | Shell ID |
| --- | --- | --- | --- |
| 22 | 32.4 | 40 | 32.4 |
| 22 | 34.4 | 42 | 34.4 |
| 22 | 36.4 | 44 | 36.4 |
| 22 | 38.4 | 46 | 38.4 |
| 22 | 40.4 | 48 | 40.4 |
| 28 | 40.4 | | |
| 28 | 42.4 | 50 | 42.4 |
| | | 52 | 42.4 |
| 28 | 46.4 | 54 | 46.4 |
| | | 56 | 46.4 |
| 32 | 46.4 | 54 | 46.4 |
| | | 56 | 46.4 |
| 28 | 50.4 | 58 | 50.4 |
| | | 60 | 50.4 |
| 32 | 50.4 | 58 | 50.4 |
| | | 60 | 50.4 |

Referring again to FIGS. 3A and 3B, the liner 300 and 302 can further comprise a fillet 316 and a chamfer 306, which transition the inner surface 308 into the liner rim 304. The combination of the fillet 316 and chamfer 306 provide a smooth transition between the generally vertical wall portion of the inner surface 308 and the rim 304 while also allowing for an increased range of motion of a femoral implant when articulated with the liner.

The rim 304 comprises a waveform pattern with wave peaks 312 and valleys 314. The waves of the liner rim waveform shape can complement the waves of the shell rim waveform shape. Optionally, the liner rim has the same number of waves as the shell rim. Moreover, the amplitude of the shell rim waves can be the same or similar to the liner rim waves.

Figure 3B:
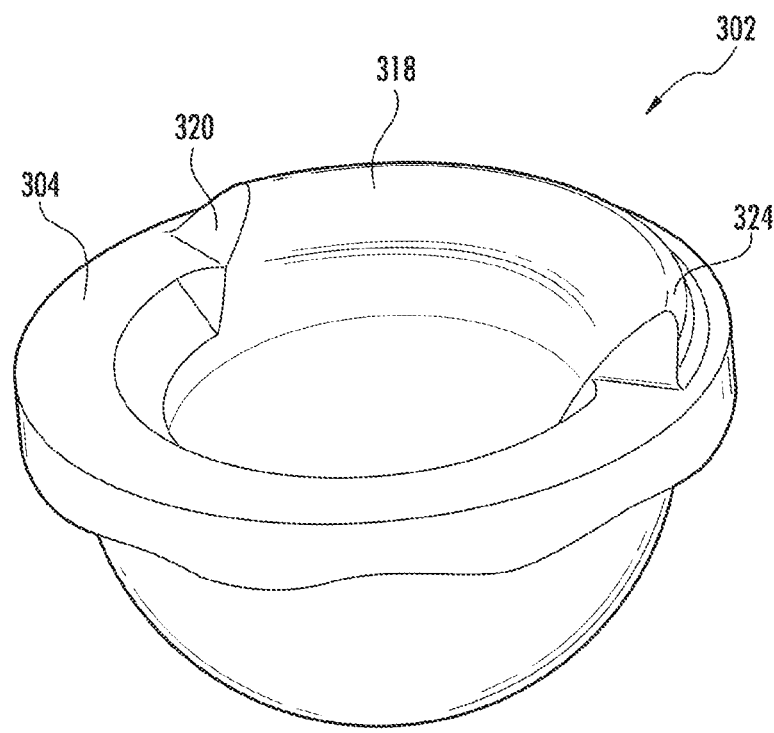

As shown in FIG. 3B, the liner 302 can further comprise a ridge 318. The ridge 318 helps prevent dislocation of a femoral implant component from the liner during use. The ridge can be positioned superiorly during surgery to restrict movement of the femoral neck such that the head of the femoral component is less likely to dislocate from the liner socket.

The ridge 318 can have a transition zone 320 on each side where the ridge 318 rises from the rim 304. The transition zone reduces sharp edges on the liner and thereby reduces the likelihood of soft tissue injury. Similarly, a rounded fillet portion 324 is positioned on the top of the ridge 318. The rounded fillet portion 324 reduces sharp edges on the liner to reduce the likelihood of soft tissue injury.

Figure 4A:
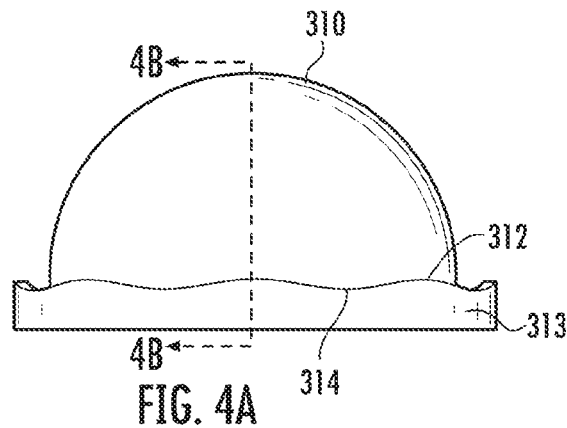
FIG. 4A is a schematic illustration of an example liner of an acetabular cup assembly.
Figure 4B:
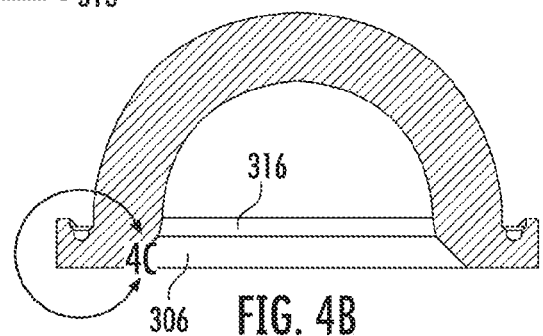
FIG. 4B is a schematic illustration of the liner shown in FIG. 4A taken across cross section 4A-4A.
Figure 4C:
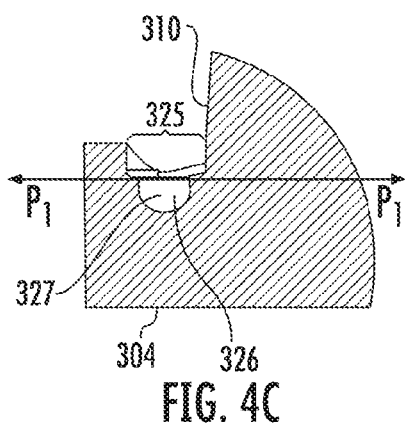
FIG. 4C is a schematic illustration showing portions of FIG. 4B in greater detail.
Figure 4D:
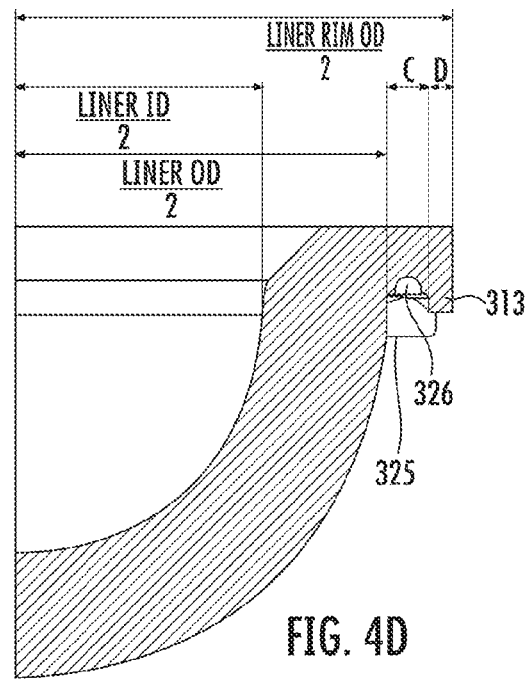
FIG. 4D is a schematic illustration showing portions of an example shell of an acetabular cup assembly.

Referring now to FIGS. 4A-C, portions of an example liner are shown schematically in further detail. FIG. 4B is a schematic cross sectional view taken across plane B-B of FIG. 4A. FIG. 4B shows the fillet 316 and chamfer 306 of the inner surface 308 of shell. FIG. 4C shows a detail of the circular section C from FIG. 4B. FIG. 4C shows a cross section of the groove 326 with a center 327. The center 327 is located below the plane $P_1$-$P_1$.

Figure 7A:
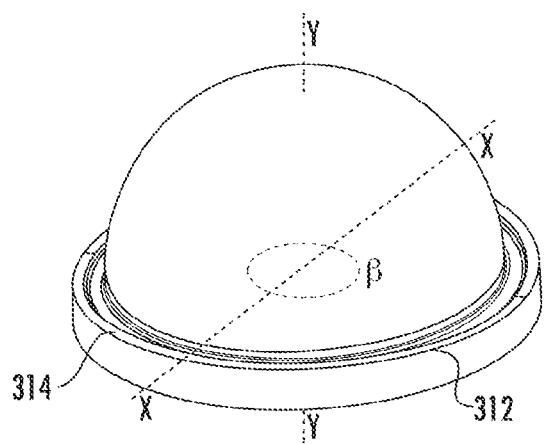
FIGS. 7A-I are schematic illustrations showing example liners having rims with a waveform shape.
Figure 7B:
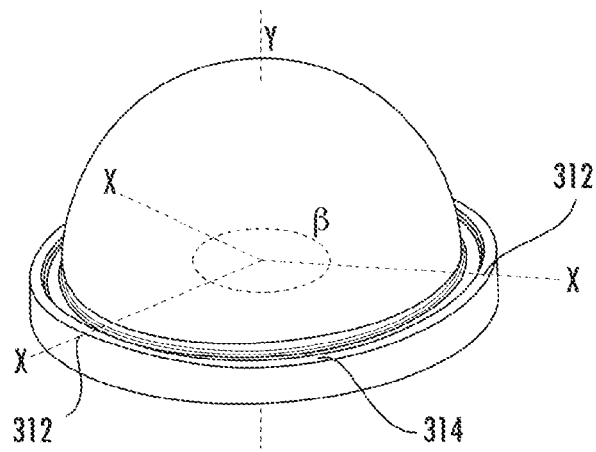
Figure 7C:
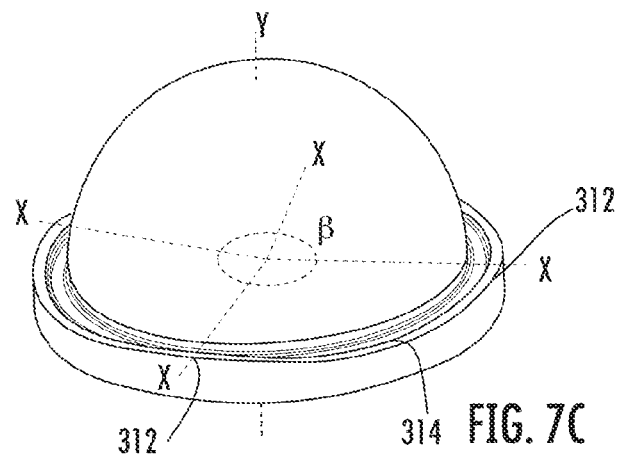
Figure 7D:
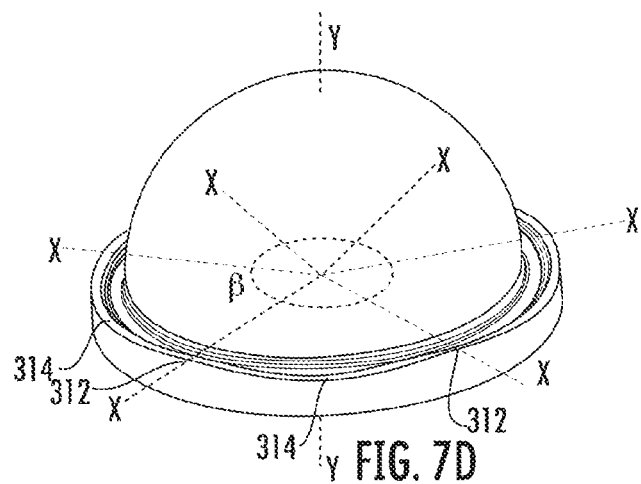
Figure 7E:
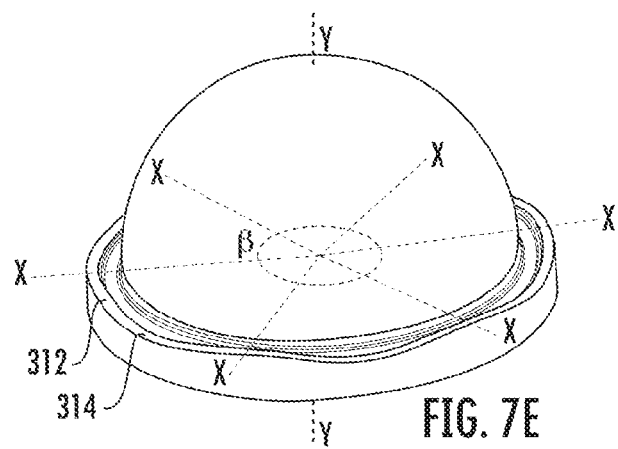
Figure 7F:
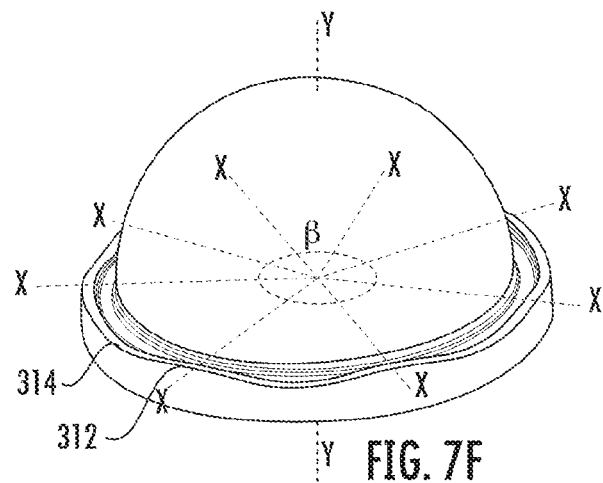

Now referring to FIGS. 7A-I, the number of wave peaks and valleys of the liner waveform can vary. Similar to the waveform of the shell, the liner wave form has peaks separated by peak to peak angle ($\beta$) relative to the axis Y-Y, which extends through the center of the liner. Thus, the angle between the peaks 312 can be determined in reference to the central axis of the shell Y-Y shown in FIGS. 7A-I. Spokes drawn perpendicular to the axis Y-Y intersect the peak 312 of each liner wave. The angle ($\beta$) denotes the angle between peaks. For example, in FIG. 7A, two peaks 312 are shown with an angle ($\beta$) of 180° between each. In FIG. 7B, a third wave peak is added with the angle between each peak ($\beta$) of 120°. In each successive example, shown in FIGS. 7C-I, an additional peak 312 is shown and the angle ($\beta$) between each peak can be determined by dividing 360° by the total number of peaks.

Figure 7G:
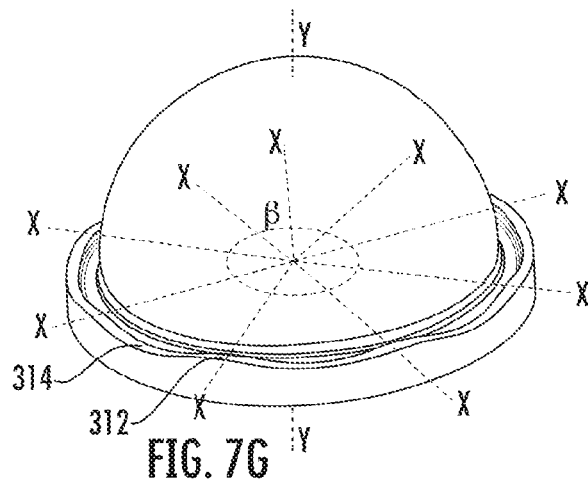
Figure 7H:
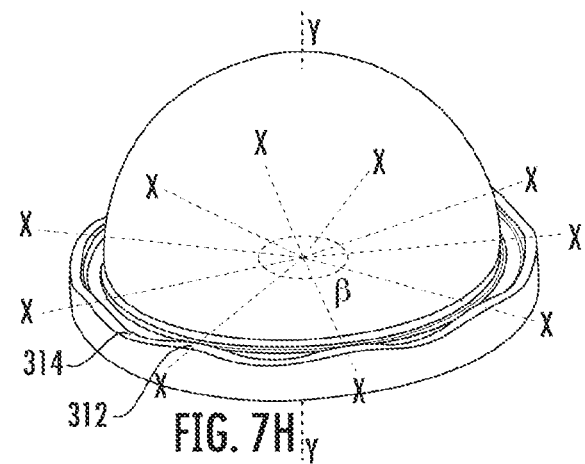
Figure 7I:
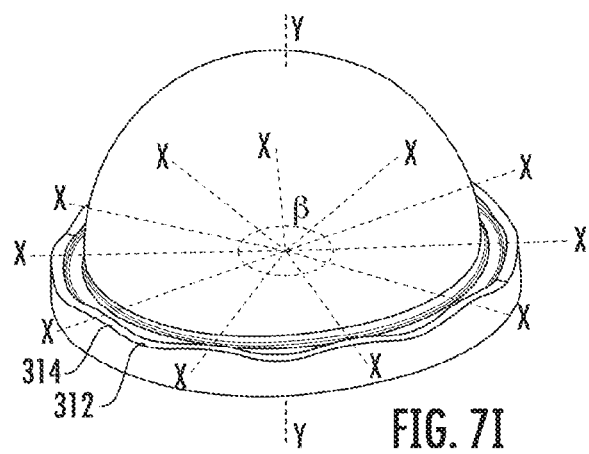

Thus, by way of example, FIG. 7G shows an example device with eight peaks. By dividing 360° by the total number of peaks, eight, the angle ($\beta$) between each peak 312 is determined to be 45°. The number of peaks can vary. Optionally, there can be two or more peaks 312. For example, there can be 2, 3, 4, 5, 6, 7, 8, 9, 10 or more peaks and the angles between the peaks can be about 180, 120, 90, 72, 60, 51.4, 45, 40, or 36 degrees. Moreover, it is not necessary for the peaks to be uniformly distributed as shown in FIGS. 7A-I. In this regard, the angle between the peaks 312 can vary. A liner can have a waveform with multiple peaks wherein the angles between one or more wave peak are the same or differs. The angles between each peak can vary from less than one degree to greater than 359 degrees. As described above, when the angle between the peaks and valleys are the same the peaks and valleys are uniformly distributed in the shell as shown in FIGS. 1A-C and in FIGS. 6A-I, and in the liner as shown in FIGS. 3A and B and in FIGS. 7A-I. In these aspects, the positioning options wherein the liner waveform is substantially congruent with the shell waveform are increased.

Figure 5A:
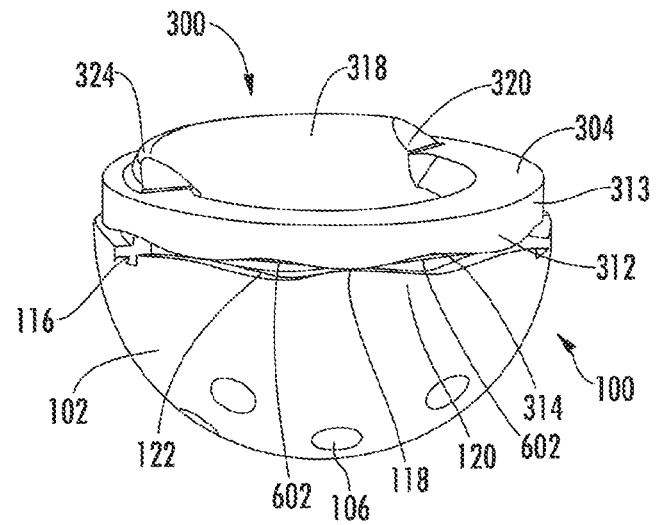
FIG. 5A is a schematic illustration showing an example liner resting in an example shell of an acetabular cup assembly in a non-aligned state.
Figure 5B:
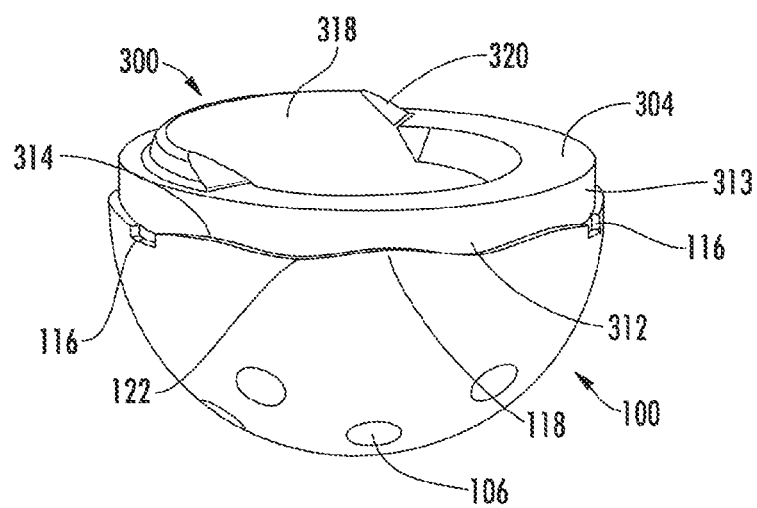
FIG. 5B is a schematic illustration showing an example liner resting in an example shell of an acetabular cup assembly in an aligned state.

Referring to FIGS. 5A and 5B, the liner 300 can be positioned within the shell 100. As shown in FIG. 5A, the liner 300 can be positioned in a non-aligned position with the shell 100. As shown in FIG. 5B, the liner 300 can be positioned in an aligned position with the shell 100. In the non-aligned position shown in FIG. 5A, the peaks 312 of the liner rim 304 waveform are not resting in the valleys 122 of the waveform in the outer rim 114. Similarly, the peaks 118 of the shell outer rim 114 waveform are not resting in the valleys 314 of the liner rim 304.

In the non-aligned position, one or more gaps 602 are located between the articulating surfaces of the shell outer rim 114 and the liner rim 304. In this position, the liner 300 and the shell 100 can be rotated relative to each other. Optionally, the liner 300 and the shell 100 can be rotated relative to each other such that the waveform surfaces of the outer rim 114 of the shell 100 and the rim 304 of the liner slide over each other until one or more peak 118 of the outer shell rim 114 rests within one or more valley 314 of liner rim 304.

The corresponding waveforms of the shell 100 and the liner 300 allow the shell and liner to be initially positioned wherein one or more valleys and peaks are not aligned as shown in FIG. 5A. The shell and liner can subsequently be rotated into an aligned position for locking. When rotated into the aligned position shown in FIG. 5B, the shell locking mechanism 110 can be positioned within the liner groove 326. The locking mechanism 110 and the groove 326 can be sized and shaped such that they snap together to form a secure bond, for example by friction fit or by distortion of the groove 326 by the locking mechanism 110. Interference caused by peak-to-peak contact prevents planar alignment of the locking mechanism and the groove and prevents secure locking until the shell and liner are respectively rotated into a peak-to-valley alignment.

The operator of the device, such as surgeon, can rotate, mate and lock the shell and the liner readily without visualizing the shell and/or the liner. The corresponding waveform of the shell and liner can facilitate proper positioning of the shell and liner during surgical approaches which limit or impede the surgeon's visual field. Moreover, the positioning of the locking mechanism 110 into the groove 326 may produce a noise audible to the operator to provide further indication that the liner 300 is locked in the shell 100. The distance the liner and shell are rotated respective to each other before mating and locking may vary depending on the period of the respective waveforms of the shell and the liner.

For example, a greater number of wave peaks and valleys, with a corresponding smaller angle between peaks, or period, may require less rotation of the liner relative to the shell before aligning and locking. Similarly, a smaller number of wave peaks and valleys, with a corresponding larger angle between peaks, or period, may require more rotation of the liner relative to the shell before alignment and locking. Thus, shells and liners with differing waveforms can be selected depending on the desired distance of rotation. If a surgeon prefers the shell and liner to rotate little relative to each other after the initial placement of the liner into the shell, a shell and liner combination having a greater number of peaks and valleys can be used relative to a shell and liner combination where more rotation is preferred before mating. When a liner with a ridge 318 is used, a larger number of peaks and valleys results in a larger number of options for rotational positioning of the ridge relative to the shell and to the patient.

When positioned in the aligned position, the aligned shell and liner waveforms provide resistance to additional rotational movement. The locking mechanism 110, when positioned within the groove 326, also provides resistance to rotational movement. Thus, the acetabular cup assembly allows the shell and liner to be guided into a position where the liner is secured in place by the interaction of the aligned waveforms and the locking mechanism 110 and groove 326. The locked shell 100 and liner 300 can be separated by placing a tool into the slot 116 and leveraging the shell 100 and liner 300 apart.

Also provided are methods of seating a liner for an acetabular prosthetic assembly within its complementary shell. An example method comprises providing an acetablular cup assembly. The assembly comprises a liner and a shell. The shell can comprise an outer shell surface adapted for seating in a subject's pelvic bone, an inner shell surface, a shell opening, and a rim positioned peripherally to the shell opening and having a waveform shape. The waveform shape can have at least one wave peak and at least one wave valley.

The liner is adapted for insertion into the shell. The liner comprises an outer liner surface, an inner liner surface, a liner opening and a rim positioned peripherally to the liner opening and having a waveform shape. The waveform shape has at least one wave peak and at least one wave valley. The liner may be inserted into the shell such that at least a portion of the liner rim rests on at least a portion of the shell rim.

For example, at least one liner wave peak can rest on at least one shell wave valley when the liner is inserted into the shell. In another example, at least one liner wave peak rests on at least one shell wave peak when the liner is inserted into the shell. Moreover, at least one liner wave peak can rest on the shell rim waveform at a location between at least one shell wave peak and at least one shell wave valley when the liner is inserted into the shell.

When the liner is inserted into the shell in a position wherein the liner peak is not seated within the shell valley, the liner can be rotated relative to the shell such that the liner wave peak moves from its resting position on the shell wave peak, or from its resting position between the shell wave peak and the shell wave valley, into a position where the liner wave peak rests within a shell wave valley. In this position, a locking mechanism can be engaged to secure the liner to the shell with the shell wave peak is located within the shell wave valley.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An acetabular cup implant, comprising:
  a shell having an outer shell surface adapted for seating in a subject's pelvic bone, an inner shell surface, a shell opening, and a rim positioned peripheral to the shell opening and having a waveform shape, the waveform shape having at least one wave peak and at least one wave valley;
  a liner adapted for insertion into the shell, the liner having an outer liner surface, an inner liner surface, a liner opening, and a rim positioned peripheral to the liner opening and having a waveform shape, the waveform shape having at least one wave peak and at least one wave valley, wherein at least a portion of the liner rim rests on at least a portion of the shell rim upon insertion of the liner into the shell; and
  a locking mechanism that is engageable upon insertion of the liner into shell in a position where one or more liner peaks rests within one or more shell valleys, wherein engagement of the locking mechanism secures the liner in the shell, and further wherein the locking mechanism protrudes vertically from the horizontal plane of the shell rim.

2. The acetabular cup implant of claim 1, wherein at least one liner wave peak rests within at least one shell wave valley when the liner is inserted into the shell.

3. The acetabular cup implant of claim 1, wherein at least one liner wave peak rests on at least one shell wave peak when the liner is inserted into the shell.

4. The acetabular cup implant of claim 1, wherein at least one liner wave peak rests on the shell rim waveform shape at a location between at least one shell wave peak and at least one shell wave valley when the liner is inserted into the shell.

5. The acetabular cup implant as in one of claim 3 or 4, in which the liner is rotatable relative to the shell.

6. The acetabular cup implant of claim 5, wherein the liner is rotated relative to the shell such that the liner wave peak moves from its resting position on the shell wave peak, or from its resting position between the shell wave peak and the shell wave valley, into a position where the liner wave peak rests within a shell wave valley.

7. The acetabular cup implant as in any one of claims 1, 2, 3 and 4, in which the shell and the liner rim waveform shapes each comprise a plurality of wave peaks and wave valleys.

8. The acetabular cup implant of claim 7, wherein each shell peak and shell valley are spaced equally about the shell rim from each neighboring shell peak or shell valley.

9. The acetabular cup implant of claim 8, wherein there are 2, 3, 4, 5, 6, 7, 8, 9 or 10 shell peaks.

10. The acetabular cup implant of claim 9, wherein each shell peak is separated from its neighboring shell peak on the shell rim by an angle measured relative to an axis of the shell that is perpendicular to the shell opening.

11. The acetabular cup implant of claim 10, wherein the angle is about 180, 120, 90, 72, 60, 51.4, 45, 40 or 36 degrees.

12. The acetabular cup implant of claim 10, wherein the angle is about 180, 120, 90, 72, 60, 51.4, 45, 40 or 36 degrees.

13. The acetabular cup implant of claim 8, wherein there are 2, 3, 4, 5, 6, 7, 8, 9 or 10 shell valleys.

14. The acetabular cup implant of claim 13, wherein each shell valley is separated from its neighboring shell valley on the shell rim by an angle measured relative to an axis of the shell that is perpendicular to the shell opening.

15. The acetabular cup implant of claim 7, wherein each liner peak and each liner valley are spaced equally about the liner rim from each neighboring liner peak or liner valley.

16. The acetabular cup implant of claim 15, wherein each liner peak is separated from its neighboring liner peak on the liner rim by an angle measured relative to an axis of the liner that is perpendicular to the liner opening.

17. The acetabular cup implant of claim 16, wherein the angle is about 180, 120, 90, 72, 60, 51.4, 45, 40 or 36 degrees.

18. The acetabular cup implant of claim 7, wherein there are 2, 3, 4, 5, 6, 7, 8, 9 or 10 liner peaks.

19. The acetabular cup implant of claim 7, wherein there are 2, 3, 4, 5, 6, 7, 8, 9 or 10 liner valleys.

20. The acetabular cup implant of claim 7, wherein each liner valley is separated from its neighboring liner valley on the liner rim at an angle relative to an axis of the liner that is perpendicular to the shell opening.

21. The acetabular cup implant of claim 20, wherein the angle is about 180, 120, 90, 72, 60, 51.4, 45, 40 or 36 degrees.

22. The acetabular cup implant of claim 1, wherein the locking mechanism is not capable of engagement when a liner peak rests on a shell peak, or when a liner peak rests between a shell peak and a shell valley.

23. The acetabular cup implant of claim 1, wherein the implant further comprises at least one slot having an opening defined by the outer shell surface and a portion of the liner.

24. The acetabular cup implant of claim 23, wherein the slot extends between the shell and liner towards the inner surface of the shell.

25. The acetabular cup implant of claim 23, wherein the slot is adapted to receive a tool to provide leverage for encouraging the liner's removal from the shell.

26. The acetabular cup implant of claim 23, wherein the portion of the liner that defines the slot is a portion of the rim.

27. The acetabular cup implant of claim 1, wherein the locking mechanism is arcuate or ring shaped.

28. The acetabular cup implant of claim 1, wherein the locking mechanism is disrupted by one or more slots.

29. The acetabular cup implant of claim 1, wherein the locking mechanism has a hump cross-sectional shape.

30. The acetabular cup implant of claim 29, wherein the hump protrudes from the inner rim.

31. The acetabular cup implant of claim 1, wherein the locking mechanism of the shell can mate with a groove of the liner.

32. The acetabular cup implant of claim 31, wherein the groove of the liner has a center that is offset from a center plane of the shell.

33. The acetabular cup implant of claim 32, wherein the groove and the locking mechanism have complementary shapes with offset centers, thereby producing a lip on the inner and outer edge of the groove opening that can made with an indention produced at a junction of the locking mechanism and inner rim.

34. A method of seating a liner for an acetabular prosthetic assembly within its complementary shell, comprising:

providing an acetabular cup assembly, the assembly comprising a liner, a shell, and a locking mechanism; wherein:

the shell comprises an outer shell surface adapted for seating in a subject's pelvic bone, an inner shell surface, a shell opening, and a rim positioned peripherally to the shell opening and having a waveform shape, the waveform shape having at least one wave peak and at least one wave valley; wherein the liner is adapted for insertion into the shell, and the liner comprises an outer liner surface, an inner liner surface, a liner opening, and a rim positioned peripherally to the liner opening and having a waveform shape, the waveform shape having at least one wave peak and at least one wave valley;

a locking mechanism that is engageable upon insertion of the liner into the shell in a position where one or more liner peaks rests within one or more shell valleys, wherein engagement of the locking mechanism secures the liner in the shell, and further wherein the locking mechanism protrudes vertically from the horizontal plane of the shell rim; and inserting the liner into the shell such that at least a portion of the liner rim rests on at least a portion of the shell rim.

35. The method of claim 34, wherein at least one liner wave peak rests on at least one shell wave valley when the liner is inserted into the shell.

36. The method of claim 34, wherein at least one liner wave peak rests on at least one shell wave peak when the liner is inserted into the shell.

37. The method of claim 34, wherein at least one liner wave peak rests on the shell rim waveform at a location between at least one shell wave peak and at least one shell wave valley when the liner is inserted into the shell.

38. The method of claim 36 or 37, wherein the liner is rotated relative to the shell such that the liner wave peak moves from its resting position on the shell wave peak, or from its resting position between the shell wave peak and the shell wave valley, into a position where the liner wave peak rests within a shell wave valley.

* * * * *